United States Patent [19]
Hollingsworth

[11] Patent Number: 6,153,724
[45] Date of Patent: Nov. 28, 2000

[54] PREPARATION OF CROSS-LINKED 2-DIMENSIONAL POLYMERS WITH SIDEDNESS FROM α,β-LACTONES

[75] Inventor: Rawle I. Hollingsworth, Haslett, Mich.

[73] Assignee: Board of Trustees Operating Michigan State University, East Lansing, Mich.

[21] Appl. No.: 09/159,305

[22] Filed: Sep. 24, 1998

[51] Int. Cl.$^7$ .......................... C08G 69/08; C08G 73/10; C08G 69/26

[52] U.S. Cl. ......................... 528/310; 528/318; 528/322; 528/335

[58] Field of Search .................................. 528/318, 310, 528/322, 335

[56] References Cited

U.S. PATENT DOCUMENTS

| | | |
|---|---|---|
| 2,274,831 | 3/1942 | Hill . |
| 2,691,643 | 10/1954 | Chirtel et al. . |
| 2,786,045 | 3/1957 | Chirtel et al. . |
| 2,968,629 | 1/1961 | Thompson . |
| 3,525,718 | 8/1970 | Derieg et al. . |
| 5,292,939 | 3/1994 | Hollingsworth . |
| 5,319,110 | 6/1994 | Hollingsworth . |
| 5,374,773 | 12/1994 | Hollingsworth . |

OTHER PUBLICATIONS

Refojo and Leong, J. Biomed. Mater. Res., vol. 15, pp. 497–509 (1981).
Corkhill et al., Biomaterials, vol. 10, pp. 3–10 (1989).
Bruck, J. Biomed. Mater. Res., vol. 7, pp. 387–404 (1973).
Vakkalanka et al., J. Biomater. Sci. Polym, Ed., vol. 8 pp. 119–129 (1996).
Yoshida, et al., J. Biomater. Sci. Polym. Ed., vol. 3, pp. 155–162 (1991).
DeMoor, et al., Biomaterials, vol. 12, pp. 836–840 (1991).
Valuev, et al., J. Biomater. Sci. Polym, Ed., vol. 5, pp. 37–48 (1993).
Zdrahala, J. Biomater. Appl., vol. 10, pp. 309–329 (1996).
Cauich–Rodriguez, et al., Biomaterials, vol. 17, pp. 2259–2264 (1996).
Osada and Matsuda, Nature, vol. 376, p. 219 (1995).
Peppas and Merrill, J. Biomed. Mater. Res., vol. 11, pp. 423–434 (1977).
Jeyanthi and Kao, Biomaterials, vol. 11, pp. 238–243 (1975).
Hoffmann, In: Polymers in Medicine and Surgey. Kronenthal (ed). Plenum Press, New York, NY., pp. 33–44 (1975).
Lotina, et al., Biomaterials, vol. 17, pp. 559–569 (1996).
Patil, et al., Biomaterials, vol. 17, pp. 2343–2350 (1996).
Llewellyn, Ann. Occup. Hyg., vol. 15, pp. 393–397 (1972).
Rogers, et al., Appl. Environ. Microbiol., vol. 60 pp. 1585–1592 (1994).
Steinmann and Havemeister, Zentralbl. Bakteriol. Mikrobiol., Hyg. B., vol. 176, pp. 546–552 (1982).
Onsoyen and Skaugrud, J. Chem. Technol Biotechnol., vol. 49, pp. 395–404 (1990).
Muzzarelli and Rocchetti, J. Chromatogr., vol. 96, pp. 115–121 (1974).

*Primary Examiner*—John Kight
*Assistant Examiner*—Raymond Covington
*Attorney, Agent, or Firm*—Ian C. McLeod

[57] ABSTRACT

Polymers and processes for synthesizing the polymers from α,β-unsaturated lactones, particularly 2(5H)-furanone, and amines with side chains. The polymers are used as hydrogels, as polymers that can bind metals and form complexes that are soluble in organic solvents, as polymers useful as flocculants in water purification, as polymers useful on non-fouling surfaces for biofilm suppression, polymers for use on non-thrombogenic surfaces, and polymers with uses as thin conductive films for microchips and other electronic devices. The process is a polymerization reaction involving the cyclic α,β-unsaturated lactone and a primary amine or primary ammonium compound.

38 Claims, 9 Drawing Sheets

$-n\ e^-$

PREPARATION OF CROSS-LINKED 2-DIMENSIONAL POLYMERS WITH SIDEDNESS FROM α,β-LACTONES

FIELD OF THE INVENTION (1) Field of the Invention

The present invention provides polymeric compositions and processes for synthesizing the polymer compositions. The process is a polymerization reaction involving a cyclic α,β-unsaturated lactone and a long chain primary amine. The polymer compositions self-assemble and can form sheets with a polar face and a non-polar face, two polar faces, or two non-polar faces wherein the "face" is defined as the opposed sides of the sheet. Preferably, the polymer compositions are polyamides synthesized from 2(5H)-furanone. The present invention further provides polymer compositions and processes for synthesizing the polymer compositions from 2(5H)-furanone for uses as hydrogels, polymers that can bind metals and form complexes that are soluble in organic solvents, polymers for use as flocculants in water purification, polymers for use on non-fouling surfaces for biofilm suppression, polymers for use on non-thrombogenic surfaces, and polymers with uses as thin conductive films for microchips and other electronic devices.

(2) Description of the Related Art

In the past, the desirable physical properties of organic polymers were simple. Of interest were ordinary attributes such as transparency, flexibility, heat and electrical conductance, water resistance, and pliability. These physical requirements could be met by any one of a wide variety of polymeric materials fabricated by one of several polymerizing reactions. These reactions include the simple polymerization of alkenes (e.g. polypropylene and polyvinylchloride), the condensation of acids and bases to form polyesters, or acids and amines to form polyamides.

More recently, there has been much effort to fabricate organic polymeric materials with more sophisticated properties. These include materials that can conduct electricity, that are magnetic, and materials that change some property such as color or refractive index under the influence of various external factors such as pressure, electric fields, magnetic fields, pH changes, or temperature alterations. In all of these applications, one critical requirement is that some functional group or groups along the polymer backbone be aligned in a regular repeating fashion with very high density. Polymeric materials with very different properties can be made depending on the choice of the functional groups. Electron donor-acceptor pairs can be conductive or have optical properties that are influenced by electric or magnetic fields. Such polymeric materials have applications in sensor devices and optical switches. An array of negatively charged groups is a typical arrangement sought for conducting organic polymers where the charge carriers are metal ions and protons. Hydrogels can be formed if charges are present on the side chains. Materials with special conductive, magnetic or electro-optical properties can be fabricated from polymers having specialized aromatic side chains.

There are several methods for introducing side chains to a main chain polymer. One strategy is to add the side chains to the preformed main chain. This is generally not satisfactory because of the lack of predictability and reproducibility of stoichiometry, under-derivitization for stearic reasons, difficulty in accessing the interior of the polymer, poor solubility of the polymer, and inefficient coupling reactions. Alternatively, the desired side chain can be attached to each polymer monomer prior to chain formation. This method is generally more efficient but the subsequent coupling of the monomers often requires activating groups to be attached to one or both coupling sites. For example, the preparation of polyesters and polyamides require that the carboxylic acid function be activated before chain formation. Afterwards, the spent activating group has to be removed from the product. Radical polymerization cannot be used for side chains that contain unsaturations or heteroatoms such as sulfur which act as quenching agents for radicals. Furthermore, side chains containing reactive groups such as carboxylic acids often have to be protected before coupling. Finally, synthesis of most polymers is dependent on fossil fuels, which is a non-renewable resource that is rapidly being depleted, and is a major import product which affects the balance of trade.

Examples of polymers that are polyamides which can be synthesized from renewable resources are set forth below. U.S. Pat. No. 2,274,831 to Hill discloses polyamides and the preparation of polyamides by polymerizing amino acids containing as a heteroatom a tertiary amino nitrogen or by reacting diamines and dibasic acids, either or both of which contain a hetero atom of tertiary amino nitrogen. U.S. Pat. No. 2,691,643 to Chirtel et al. discloses preparation of polypeptides of beta-alanine and amide forming derivatives of beta-alanine, beta-alanine alkyl esters, beta-alanine amides by self-condensation to produce water insoluble polypeptides which are useful for forming synthetic edible films. U.S. Pat. No. 2,786,045 to Chirtel et al. discloses polymers of hydroxyacyl-amino acids and their polymers for the preparation of tough, elastic fibers and films. U.S. Pat. No. 2,968,629 to Thompson discloses a method of inhibiting metal corrosion using a condensation product of beta-lactone. U.S. Pat. No. 3,525,718 to Derieg et al. discloses a process for producing a polyamide resin from beta-lactone. The process consists of reacting beta-lactone under anhydrous conditions at reduced temperatures to produce an amino acid addition product, and then in a subsequent step subjecting said product to polymerization conditions at elevated temperatures in which said product is substantially dehydrated to form a polyamide resin which is linear without side chains. The resin has properties that suggest it may be used in applications where nylon and Dacron have been used. All of the abovementioned inventions disclose processes to make a specific product. None of the above mentioned inventions disclose processes for synthesizing a wide variety of polymers with distinct properties.

Therefore, there is still a need for a good general method that allows the assembly of a continuous array of side chains along a polymer backbone in a quick and efficient manner. The preferred method is one that does not require activation of groups of the monomer(s), does not produce any by products that have to be eliminated, that proceeds under mild conditions, that is compatible with a large spectrum of functional groups including alcohols, acids, phosphate groups, sulfonates, nitrites, amides and amines, and which can be carried out in a wide variety of solvents from aprotic solvents to water. Because most polymers are derived from fossil fuels which are a limited resource and a resource that for the most part is imported, there is a need for said polymers be derived from renewable resources.

SUMMARY OF THE INVENTION

The present invention provides a process for the preparation of polyamide polymers from α,β-unsaturated lactone and an amine selected from the group consisting of $RNH_2$, RNH$_3^+$ and mixtures thereof which can optionally be substituted in R with heteroatoms such as O, N, S and combinations thereof which allow the formation of a polyamide polymer wherein each of the R can be the same or different and separating the polyamide polymer from the reaction mixture, wherein multiple of the R are in vertically aligned spaced relationship along a backbone formed by the polyamide.

The present invention particularly provides a process for producing polymers using α,β-unsaturated gamma-lactone (2(5H)-furanone or butenolide) as an agent to effect the regular, sequential alignment of side chains along a polyamide backbone.

The polymers prepared according to the present invention can have side groups selected from the group consisting of alkyl, alkene, alkyne, cycloalkyl, aryl, aralkyl, hydroxyl, nitrile, carboxyl, sulfate, phosphate, sulfonyl, trialkylammonium, amino acids, carbohydrates and combinations thereof.

The present invention further provides polymer compositions which are made from α,β-unsaturated lactones, an example being 2(5H)-furanone, and an amine selected from RNH$_2$ and RNH$_3^+$ or combinations thereof, according to the process of the present invention. The polymers of the present invention are two-dimensional polymers that can be used as conductive polymers, for binding metals to form complexes which are then soluble in organic solvents for sequestering or forming thin conductive films for electronic devices, for forming hydrogels with high water capacity for medical and new mechano-electrical applications, and coating surfaces for biofilm suppression, and rendering surfaces non-thrombogenic and non-hemolytic.

Objects

It is an object of the present invention to provide polyamide polymers with side chains derived from α,β-unsaturated lactones and an amine.

Another object of the present invention is to provide polymer compositions which can form sheets with a polar face and a non-polar face, two polar faces, or two non-polar faces.

A further object of the present invention to provide polymer compositions synthesized according to the present invention which can be used as hydrogels, for binding metals, for coating surfaces to make the surface hydrophobic or hydrophilic, and for forming conductive films.

It is also an object of the present invention to provide a process for the preparation of such polymers with side chains derived from α,β-unsaturated lactone and an amine.

Further still, it is an object of the present invention to provide a process for synthesizing polymeric compositions that can self-assemble to form sheets with a polar face and a non-polar face, two polar faces, or two non-polar faces.

These and other objects will become increasingly apparent by reference to the following description and the drawings.

DETAILED DESCRIPTION OF THE DRAWINGS

FIGS. 1A to 1E show the various polymeric (polyamide) compositions that can be synthesized by the process of the present invention. 1A shows a stabilized lamellar sheets in which the polar headgroups are part of the polyamide chain. 1B shows a polyamide with polyacetylene side chains capable of being conjugated to form a π-conducting sheet. 1C shows a polyamide with crown ether side chains for metal complexation. 1D shows a polyamide with amine groups for metal complexation. 1E shows a polyamide with carboxylate groups for metal complexation.

FIG. 4A is formed at a water/ether interface and visualized by phase contrast microscopy (X10) FIG. 4B is a polarized light micrograph of the two-dimensional sheet.

Figure 6:
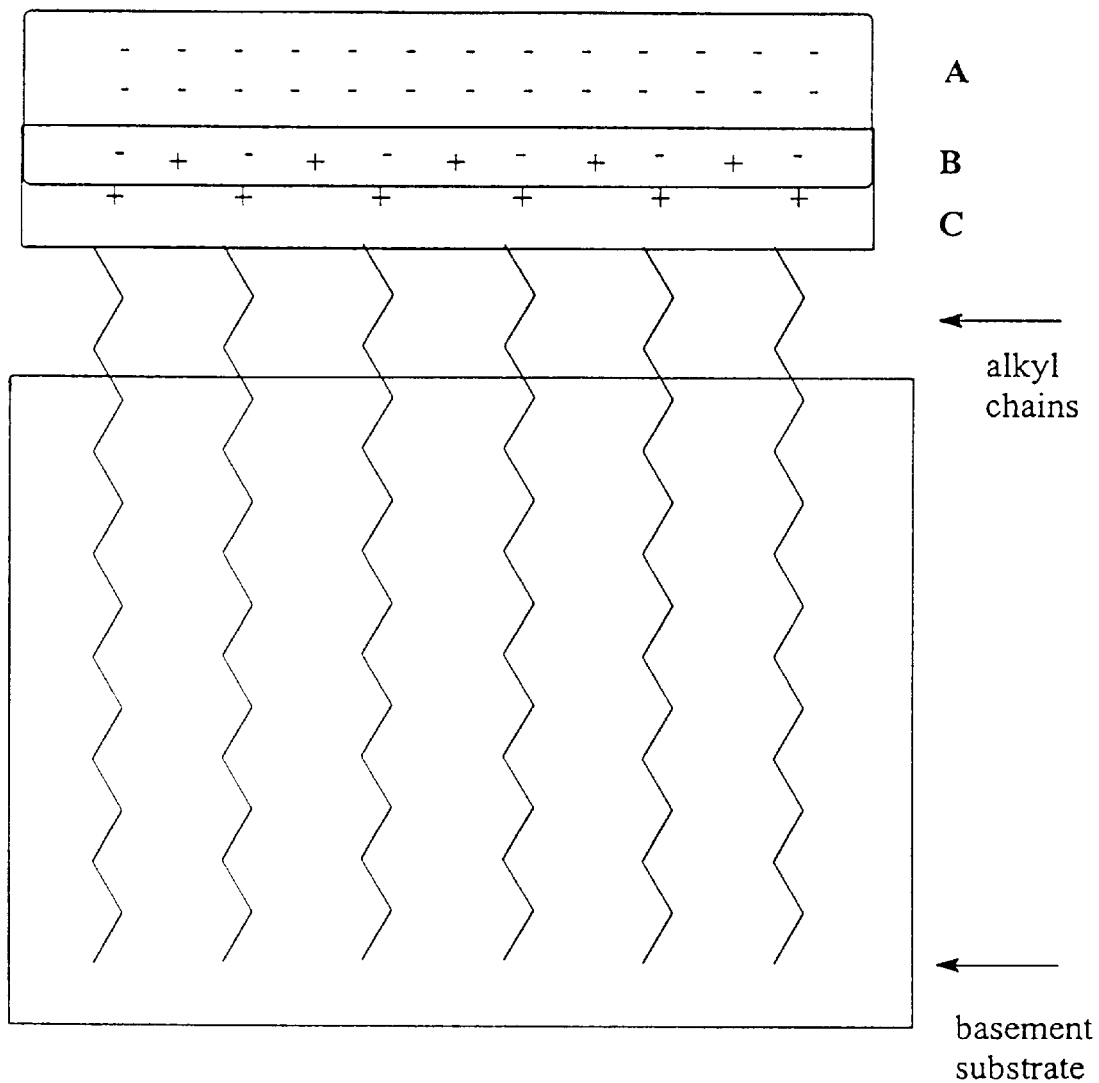

FIG. 6 shows the structure of an interpenetrating hydro gel system wherein the alkyl chains of the two-dimensional polymer are anchored to the hydrophobic face of the hydrophobic substrate (basement substrate) with the polar heads of the polymer forming a hydrogel. An interpenetrating gel matrix comprising the anionic heparin gel and the cationic gel is formed. In the Figure, A) represents the anionic heparin gel layer, B) represents the interpenetrating gel matrix layer, and C) represents the cationic gel layer.

Figure 7:
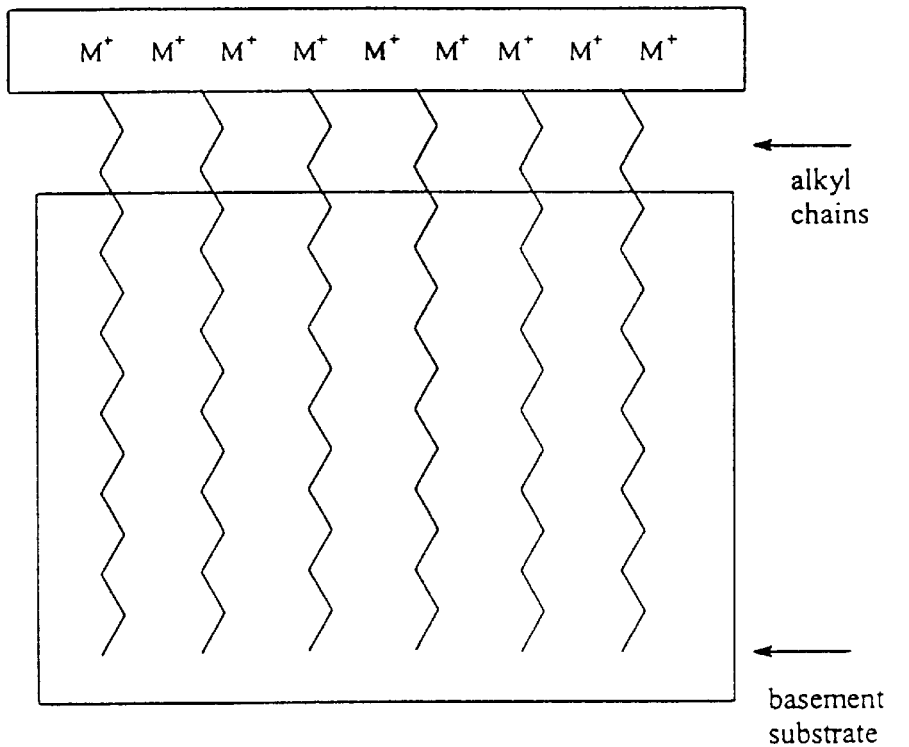
Figure 7:
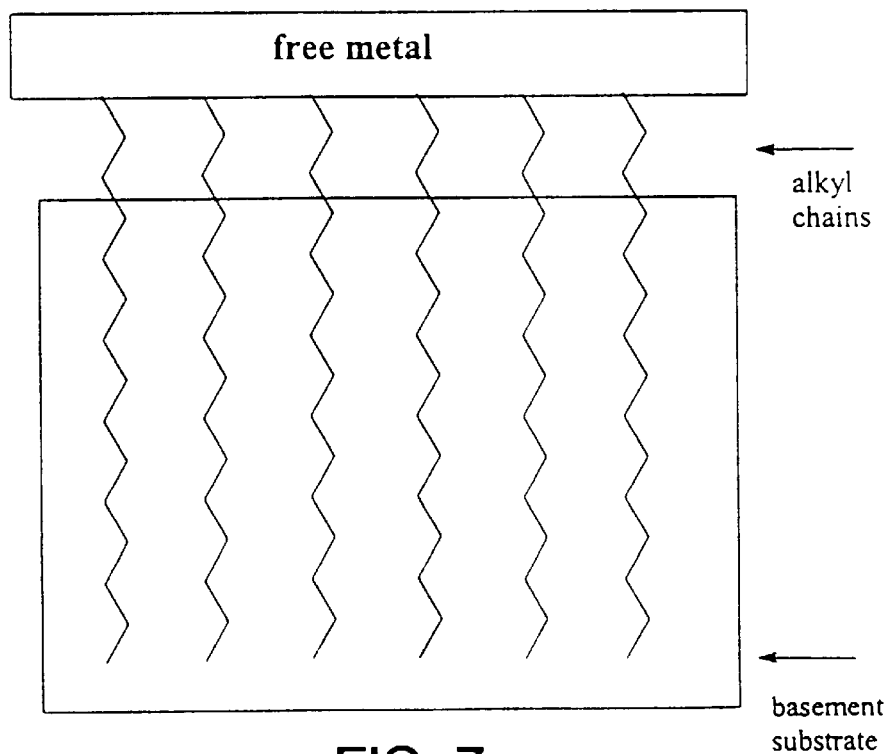

FIG. 7 shows the structure of a two-dimensional polymer gel bound to metal ions (M$^+$) which is then reduced to the free metal.

DETAILED DESCRIPTION OF THE INVENTION

The present invention provides a polyamide prepared by reacting an α,β-unsaturated lactone with an amine selected from the group consisting of RNH$_2$ and RNH$_3^+$ or mixtures thereof, wherein R is between 1 and 50 carbon atoms alone and is optionally substituted with oxygen, nitrogen, sulfur, phosphate or other groups and combinations thereof, wherein multiple of the R are in vertically aligned and spaced relationship along a backbone forming the polyamide. In the composition of the present invention the R is selected from the group consisting of alkyl, alkene, alkyne, cycloalkyl, aryl, aralkyl, hydroxyl, nitrile, carboxyl, sulfate, phosphate, sulfonyl, trialkylammonium and combinations thereof and the R groups can further be optionally substituted with a halogen selected from the group consisting of chlorine, iodine, bromine, and fluorine.

The present invention particularly provides a polymer composition that is a polyamide with the formula:

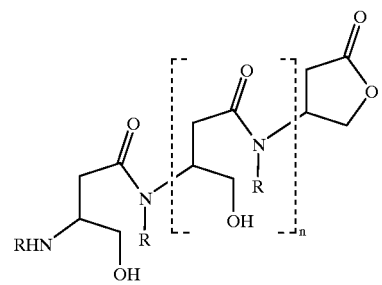

wherein n is between about 50 and 10,000, wherein R is between 1 and 50 carbon atoms alone and is optionally substituted with oxygen, nitrogen, sulfur, or phosphate and combinations thereof, wherein multiple of the R are in a vertically aligned spaced relationship along a backbone forming the polyamide and wherein R can be positively or negatively charged. In the polymer composition, the R is selected from the group consisting of alkyl, alkene, alkyne, cycloalkyl, aryl, aralkyl, hydroxyl, nitrile, carboxyl, sulfate, phosphate, sulfonyl, trialkylammonium and combinations thereof and the R groups can further be optionally substituted with a halogen selected from the group consisting of chlorine, iodine, bromine, and fluorine.

In one embodiment of the polymer composition the alkyl contains one to thirty carbon atoms. In another embodiment, the R is an alkenyl polyamine group. In still another embodiment the R is a pentaethyleneyl hexamine group and in a further still embodiment of the composition, the R is a mixture of alkyl and alkenyl groups.

The present invention further provides a process for the preparation of polyamide polymers from α,β-unsaturated lactone and an amine selected from the group consisting of $RNH_2$, $RNH_3^+$ and mixtures thereof which can optionally be substituted with oxygen, nitrogen, sulfur, phosphate and combinations thereof which allow the formation of a polyamide polymer wherein each of the R can be the same or different and separating the polyamide polymer from the reaction mixture, wherein multiple of the R are in vertically aligned spaced relationship along a backbone formed by the polyamide. In the process of the present invention the R is selected from the group consisting of alkyl, alkene, alkyne, cycloalkyl, aryl, aralkyl, hydroxyl, nitrile, carboxyl, sulfate, phosphate, sulfonyl, trialkylammonium and combinations thereof and the R groups can further be optionally substituted with a halogen selected from the group consisting of chlorine, iodine, bromine, and fluorine.

The present invention particularly provides a process for the preparation of a polymer composition that is a polyamide wherein the process comprises reacting in a reaction mixture 2-(5H)furanone and a primary amine selected from the group consisting of $RNH_2$, $R_2NH$, $RNH_3^+$ and mixtures thereof, wherein R contains between 1 and 50 carbon atoms alone and is optionally substituted with oxygen, nitrogen, sulfur, and phosphate and combinations thereof which allow the formation of a polyamide polymer in the reaction mixture of the formula:

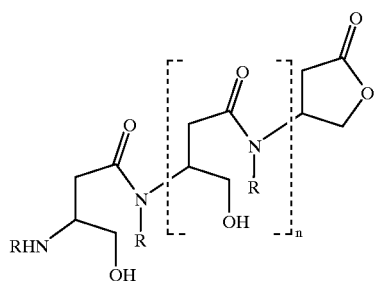

wherein n is between 50 and 10,000; and separating the polyamide polymer from the reaction mixture, wherein multiple of the R are in vertically aligned spaced relationship along a backbone formed by the polyamide. In the process of the present invention the R is selected from the group consisting of alkyl, alkene, alkyne, cyclical, aryl, aralkyl, hydroxyl, nitrile, carboxyl, sulfate, phosphate, sulfonyl, trialkylammonium and combinations thereof and the R groups can further be optionally substituted with a halogen selected from the group consisting of chlorine, iodine, bromine, and fluorine.

In one embodiment of the process of the present invention, the R is an alkyl group containing one to eight carbon atoms and the reaction is conducted in the absence of a solvent for the primary amine. In a second embodiment of the process of the present invention, the R is an alkyl group containing nine to thirty carbon atoms and the reaction is conducted in the presence of a solvent for the primary amine. In a preferred embodiment, the solvent is toluene.

In another embodiment of the process of the present invention the primary amine is an alkylene polyamine and the reaction is conducted in the presence of a solvent for the alkylene polyamine. When the alkylene polyamine is pentaethylene hexamine, the preferred solvent is selected from the group consisting of ethanol, a low-molecular weight alcohol, water containing tetrahydrofuron and water containing dioxane.

In still another embodiment of the process of the present invention, the alkylene polyamine is admixed with an alkylamine in the reaction mixture. When the alkylene polyamine is admixed with an alkylamine in the reaction mixture, the preferred solvent is selected from the group consisting of chloroform and toluene A.

One of the major tasks facing the chemical industry is the identification and development of high volume, renewable, commercially viable raw materials that can replace in large part the chemical industry's reliance on oil-based materials for manufacture of plastics, chemicals, and polymers.

The focus of the present invention is a process for preparing a variety of new polymer or polyamides with unusual and unique properties starting from α,β-unsaturated lactones such as 2(5H)-furanone. U.S. Pat. Nos. 5,292,939; 5,319,110 and 5,374,773, all to Hollingsworth and herein incorporated by reference, a process is disclosed which utilizes a hexose source such as lactose for the synthesis of 2(5H)-furanone. The inventor has discovered that 2(5H)-furanone can be used in a process to make polyamides or polymers which process and polymers are the object of the present invention. Polymers derived from lactose have the appeal that they are derived from a renewable resource. The chemical functionalities which can be imparted to polymers derived from 2(5H)-furanone are many. The chemical functionality available from 2(5H)-furanone compliments that obtained from alkenes such as propylene, ethylene, acrylic acid, acrylonitrile, and styrene, all of these are very common monomers used to make polymers.

Figure 1A:
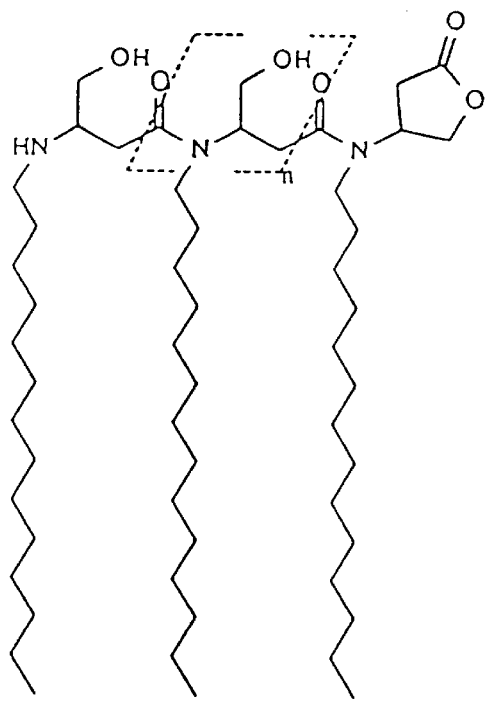
Figure 1B:
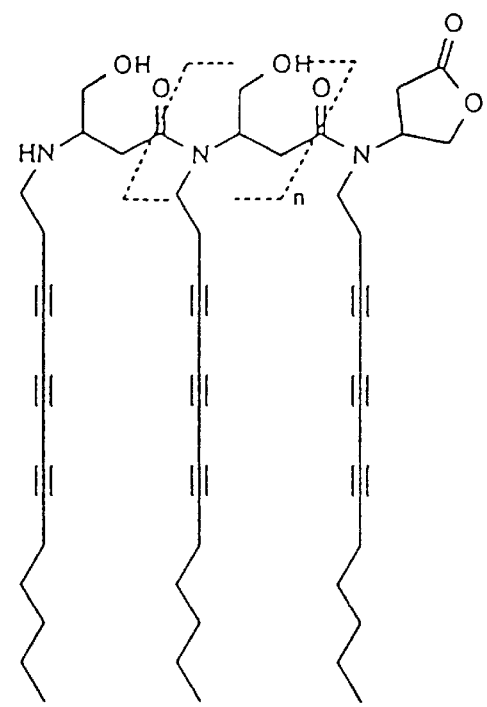
Figure 1C:
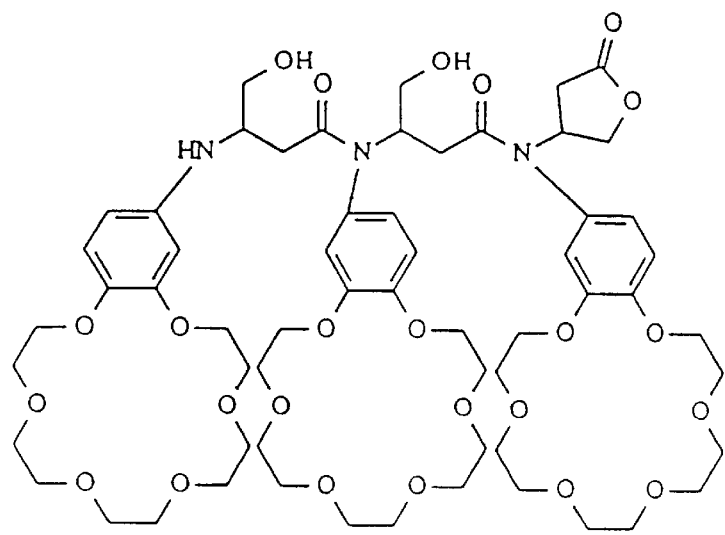

Condensation of 2(5H)-furanone with a variety of monofunctional or bifunctional amines followed by ring opening of the resulting lactone to give polyamides is an object of the present invention. Using the method of the present invention, cationic as well as anionic and neutral polymers can be made which are dependent on the nature of the side group (R). The R group can also be very long alkyl chains which generates bipolar monolayer structures in which the head group is part of a polyamide chain (FIG. 1A). The R group can also be a molecular system with special optical or electrical properties (FIG. 1B), crown ethers (FIG. 1C), polyamines with high metal complexation or ion-capture properties (FIG. 1D) or carboxylates with cation exchange or capture properties (FIG. 1E). Examples of uses for such polymer compositions prepared according to the method of the present invention are thin films for electronics through organic conductors, hydrogels, flocculants, nanostructures, and high-capacity ion exchange resins for use in precious or toxic metal recovery and water purification or reclamation. Therefore, the present invention is a process for synthesizing highly functionalized and functionalizable new polymeric materials capable of a wide variety of uses from starch or lactose derived monomers. The ability of the present invention for forming charged, neutral, hydrophobic, hydrophilic, electro-active, optically active, magnetically active or other types of polymers from one generalized reaction parallels the well-known radical polymerization of propylene, ethylene, acrylic acid, acrylonitrile, styrene, and other alkenes to form polymers with different physical properties. The present invention represents a departure for polymer chemistry from reliance on fossil fuels towards a direction in which agriculturally-derived materials are used as the primary building block. Furthermore, the present invention provides processes for the synthesis of new and novel polymer compositions. The polymers of the present invention, when having an R group, form two-dimensional polymers which means that one end of the polymer, the headgroup which forms the backbone, is different from the other end, the R group which forms the side chains.

The present invention also provides an opportunity to integrate biopolymers within the polyamide frameworks such as incorporation of biopolymers including but not limited to starch, chitin, chitosan, or cellulose into the reaction mixtures to achieve grafting or bonding. Furthermore, the functionalities present provides some measure of biodegradability for the polymers according to the present invention.

Applications for the polymer compositions of the present invention are, but are not limited to, 1) thin conductive films for electronic or electromagnetic devices, 2) hydrogels with high water capacity for medical and new mechanical-electrical applications, 3) conductive polymers, 4) polyamino-polyamides for metal recovery, and for use as a flocculant in water purification, 5) non-fouling surfaces for biofilm suppression, 6) non-thrombogenic surfaces, and 7) as micelles or liposome or adjuvants for drug delivery.

The polymerization reaction of the present invention involves a cyclic α,β-unsaturated gamma-lactone and a long chain primary amine. The long alkyl chains stack in a parallel manner and are held together by hydrophobic forces thereby forming an extended two-dimensional sheet. The terminus of the alkyl chain can be a saturated alkyl group such as methyl, isopropyl or isobutyl group or it can be a polar group, such as hydroxyl, nitrile, or amide, or an unsaturated function such as an alkene, acetylene or aryl group. Furthermore, the group can be any functionality that does not interfere with reaction of the amino group with the α,β-unsaturated gamma-lactone. These functionalities can also appear at any position along the alkyl chains thereby giving the polymers special properties such as a band of polar groups (in the case of hydroxyl functions) or a band of stacked π functions (in the case of alkenes, acetylenes, or arenes). These polymer compositions can be used for light or electron conduction or for conferring special magnetic or optical properties or for further polymerization. The polymers can be ordered by allowing them to form at the interface between a polar and a non-polar layer, e.g. the interface between water and ether. The polymers can be used to replace Langmuir Blodgett layers in most applications since the hydroxyl groups on the polar faces can be converted to a wide variety of functionalities by standard chemical techniques. These include but are not limited to acids, esters, amines, amides, nitrites, phosphates, phosphonates, sulfate, thiol, and halo groups.

The present invention particularly uses an α,β-unsaturated gamma-lactone (2(5H)-furanone or butenolide) as an agent to effect the regular, sequential alignment of side chains along a polyamide backbone. The method is based on the reactivity of the furanone which undergoes facile reaction with a primary amine by Michael-type addition to yield α,β-amino gamma-lactone which then polymerizes to form a polyamide chain with the pendant side chain. Depending on the side group (R), the method of the present invention can produce many different types of new compositions.

When the R group is a saturated long-chain alkyl group, two-dimensional polymer compositions in which the hydrophobic alkyl chains are on one face and the polar hydroxymethyl groups on the other face are fabricated. Two-dimensional polymer compositions are prepared according to the method of the present invention by heating one equivalent of furanone with the appropriate primary amine. To prepare polymer compositions with shorter chain amines that are liquid no solvent is needed except that dilution with a high boiling point solvent such as toluene is preferred. To prepare compositions with longer chain amines which are solids, tetradecylamine is an example, a solvent is required to dissolve the longer chain amine. The polymer compositions prepared according to the method of the present invention can be used for coating plastics to render the plastics hydrophilic. The free hydroxyl groups on one side of the polymer compositions can be used as sites for functionalization for further surface modifications. The R group can be polar or neutral and can range in size from a simple alcohol to a complex carbohydrate residue. When the R group is a carbohydrate, the polymer compositions tend to form stable gels in aqueous solution to form the polymer composition that is a two-dimensional polymer.

When the R group is derived from an amino acid with a neutral or anionic side chain or is an alkyl phosphate, sulfonate, or phosphate, the polymer compositions are anionic. Anionic polymer compositions are prepared according to the method of the present invention by heating one equivalent of furanone with the appropriate amino acid in water or water/ethanol in the presence of sufficient base to deprotonate the amino group to form the polymer composition that is an anionic polymer.

When the R group is a polyamine such as pentaethylene hexamine, the polymer compositions are cross-linked cationic elastomers. Cross-linked cationic elastomer polymer compositions are prepared according to the method of the present invention by heating one or 0.5 equivalents of furanone with the appropriate polyamine in ethanol to form the polymer composition that is a cross-linked elastomer.

When the R group is a mixture of a long chain aliphatic primary amines and polyamines, the polymer composition is soluble in an organic solvent but can complex metal ions and anions. The metal binding polymer composition allows solubilization of metal ions such as copper II, gold I, silver I, nickel I, and iron II and III in solvents such as chloroform or toluene.

Figure 2:
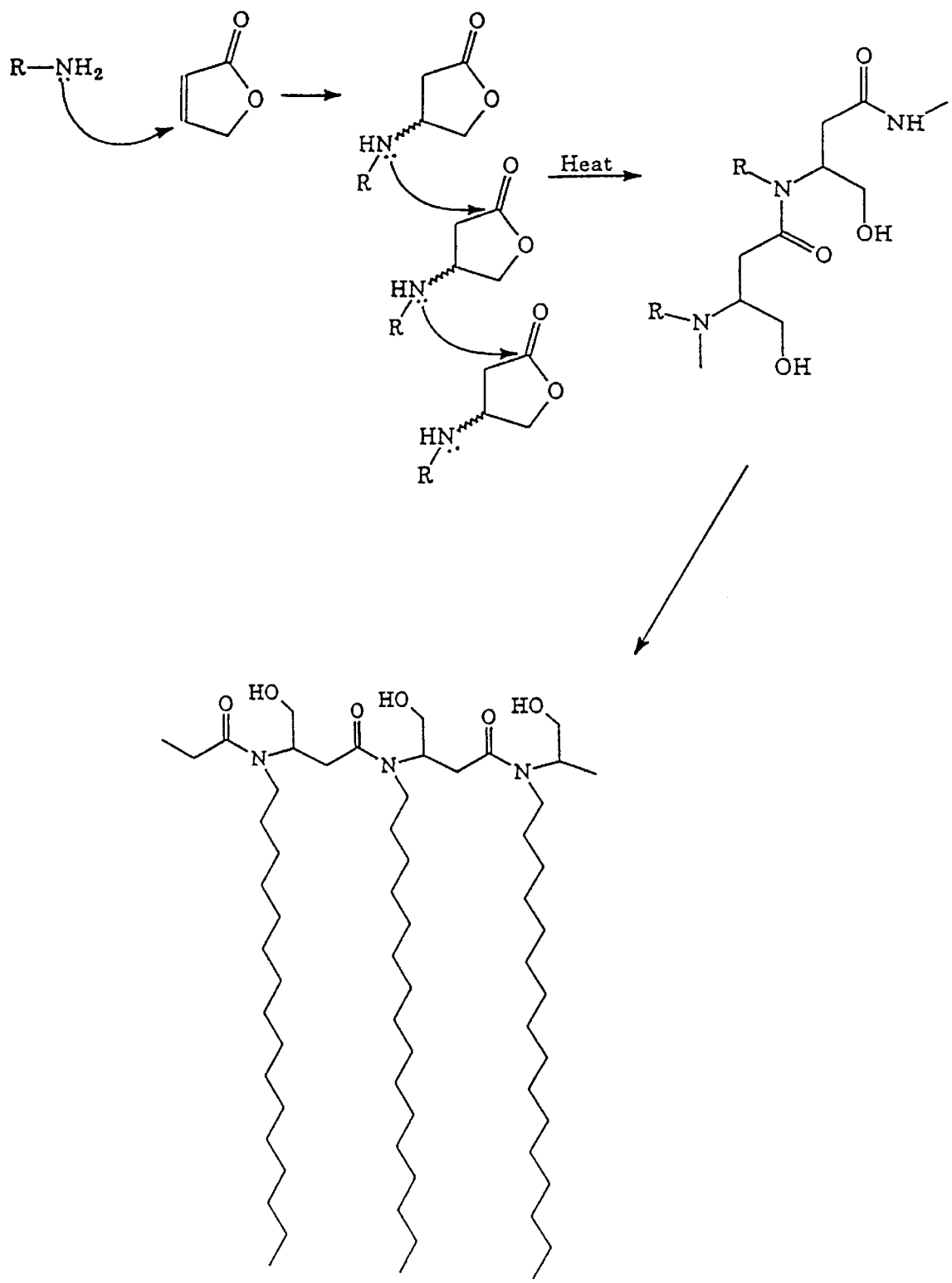
FIG. 2 shows the process for synthesizing polymeric compositions from 2(5H)-furanone according to the preferred process of the present invention.
Figure 3:
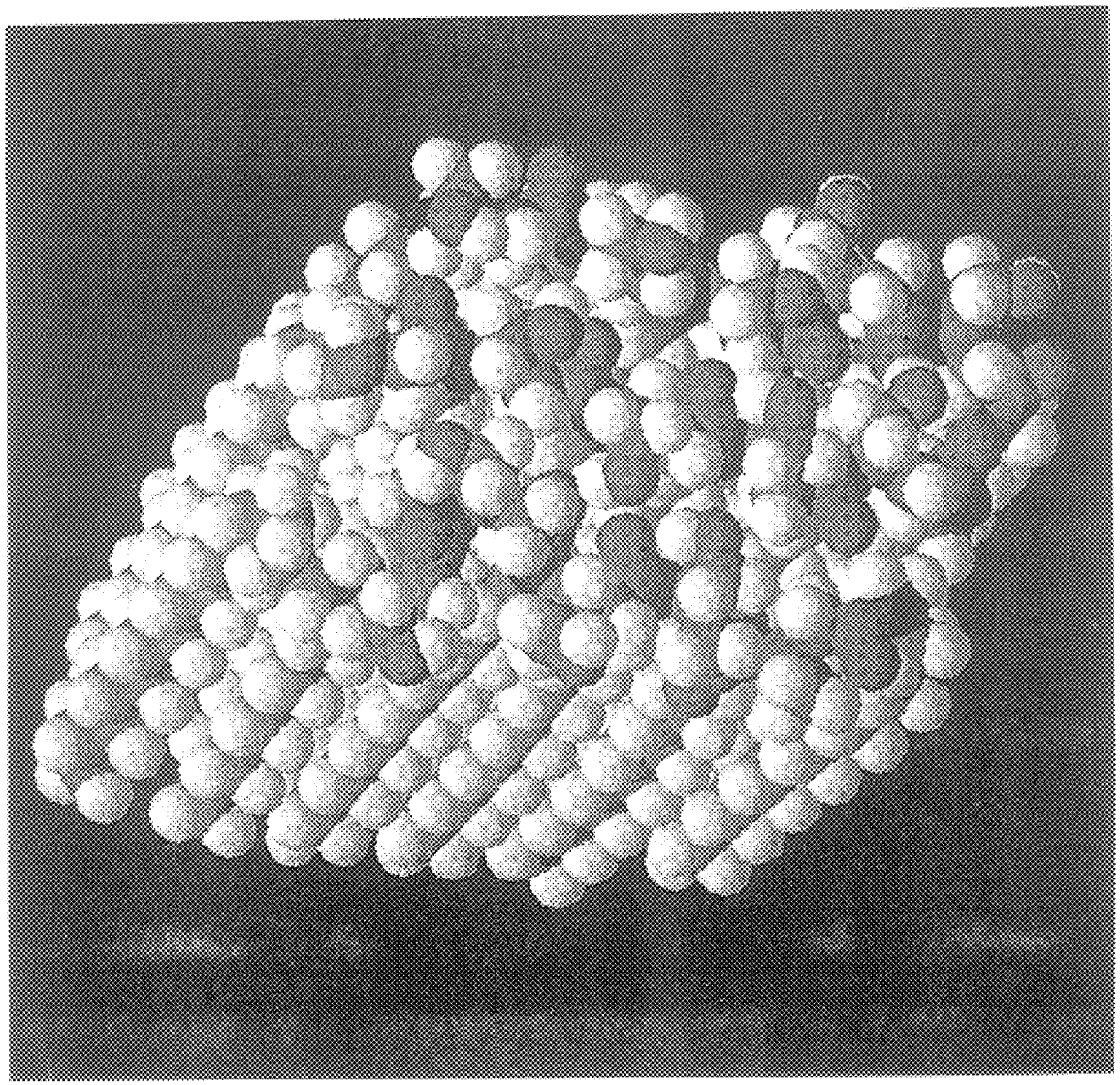
FIG. 3 shows a space filling model which shows the organization of the hydrocarbon chains and polar groups in the two-dimensional polymers (polyamides) formed by using long chain alkylamines as described in the present invention.

The present invention has established the general conditions for adding amines to 2(5)-furanone to yield polyamides. The mechanism for the reaction is shown in FIG. 2. Reaction of 2(5)-furanone with a long chain primary amine yields polyamides with structures similar to that shown in FIG. 1A. The molecular weight of the polyamides can be controlled by adjusting the temperature and time for which the amine and 2(5)-furanone are reacted. By dissolving the polymer in a non-polar solvent such as ether and floating the ether solution on water while allowing the ether to evaporate, a polymer sheet is formed (FIG. 3) which has been shown by polarized light microscopy to be highly oriented (FIG. 4). The present invention also allows the properties of the polymer compositions to be altered by controlling the degree of polymerization (average molecular weight), the length of the hydrocarbon chain (R group), the degree the hydrocarbon chain is unsaturated, and combinations thereof.

The polymers of the present invention are completely new materials in the art of polymer chemistry. The polymers are two-dimensional sheets having a hydrophobic face and a hydrophilic face which have uses such as modifying the properties of the surfaces of plastics to increase wettability or biocompatibility, or waterproofing hydrophilic surfaces. Polymers that can waterproof of hydrophilic surfaces is an important application for the present invention. For example, paper is the dominant material for the fabrication of disposable plates and cups and other similar products and for wrapping. Treatment of paper products with certain polymers of the present invention that will make them non-wettable would reduce reliance on the use of non-degradable plastics. The ability to control the surface properties of diverse materials with the polymers of the present invention is an important advance in material and surface science. For example, by using polyunsaturated alkyl groups as the side chain (R group), a continuous two-dimensional sheet of π-systems are made, making it possible to fabricate planar materials with a conducting or optically active π-band for use in electronic devices such as carbon-based microchips or display devices.

Figure 1D:
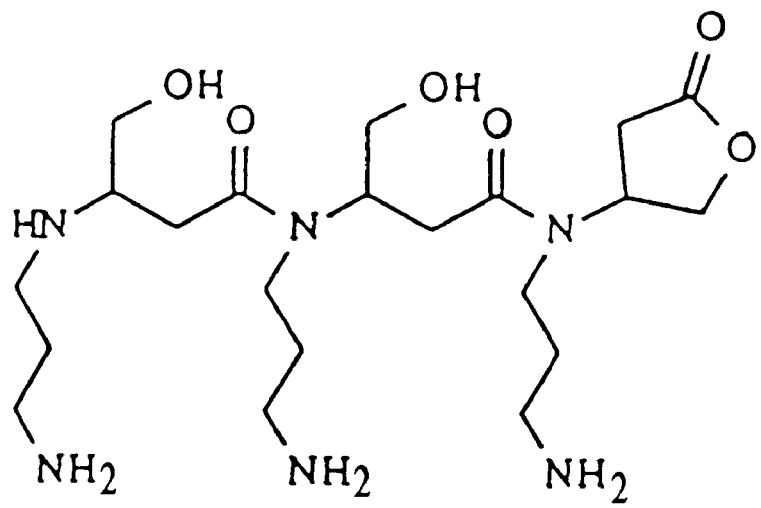
Figure 1E:
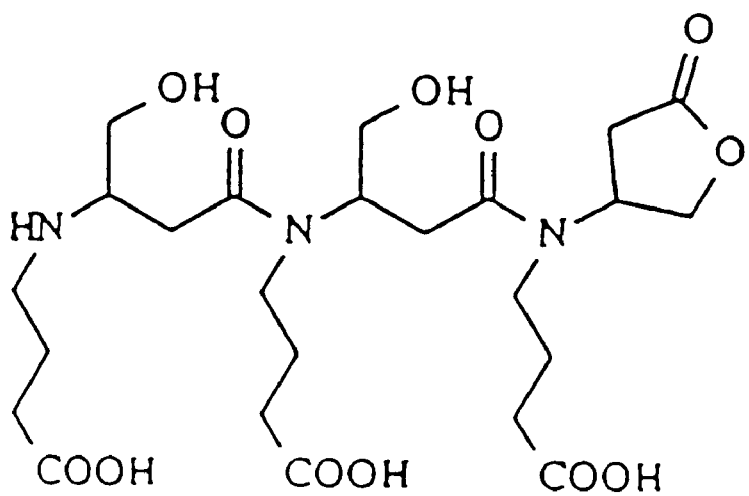

Hydrogels can be made according to the present invention by synthesizing polyamides with structures as shown in FIG. 1D which when the pH is adjusted to a low value, the polyamides become highly charged and readily form stable hydrogels which can hold many tens of times their weight of water. The properties of the hydrogels made according to the present invention can be controlled by adjusting the pH, the ionic strength of the solution, and the number of amino acids per side chain.

Hydrogels are an important material with a wide variety of uses which include artificial tissue(Refojo and Leong (1981). J. Biomed. Mater. Res., vol. 15, pp. 497–509), surgical implants (Corkhill et al. (1990). Proc. Inst. Mech. Eng., vol. 204, pp. 147–155), contact lens materials (Corkhill et al. (1989). Biomaterials, vol. 10, pp. 3–10; Bruck (1973). J. Biomed. Mater. Res., vol. 7, pp. 387–404), grafting of foreign materials to tissue (Salter and Kell (1991). Curr. Opin. Biotechnol., vol. 2, pp. 385–389), simple drug delivery vehicles (Kim et al. (1992). Pharm. Res., vol. 9, pp. 283–290), smart drug delivery vehicles that respond to temperature or pH (Vakkalanka et al. (1996). J. Biomater. Sci. Polym. Ed., vol. 8, pp. 119–129; Yoshida et al. (1991). J. Biomater. Sci. Polym. Ed., vol. 3, pp. 155–162; DeMoor et al. (1991). Biomaterials, vol. 12, pp. 836–840), enzyme immobilization matrices for biotechnological applications (Valuev et al. (1993). J. Biomater. Sci. Polym. Ed., vol. 5, pp. 37–48), in vascular grafts (Zdrahala (1996). J. Biomater. Appl., vol. 10, pp. 309–329), in composites (Cauich-Rodriguez et al. (1996). Biomaterials, vol. 17, pp. 2259–2264), and as mechanical-electrical substances Osada and Matsuda (1995). Nature, vol. 376, pp. 219). Hydrogels are primarily polymeric compositions that can retain a very high proportion of water. A basic structural feature of hydrogels is that the polymer backbone is hydrophilic and often charged. The hydrophilicity ensures good solvation and the charged groups cause the framework to expand because of repulsion of like charge. Presently, synthesis of hydrogels usually involve vinyl alcohol (Mongia et al. (1996). J. Biomater. Sci., vol. 7, pp. 1055–1064; Peppas and Merrill (1977). J. Biomed. Mater. Res., vol. 11, pp. 423–434), hydroxymethyl acrylate (Jeyanthi and Kao (1990)., Biomaterials, vol. 11, pp. 238–243; Hoffmann (1975). In: *Polymers in Medicine and Surgery*. Kronenthal (ed). Plenum Press, New York, N.Y., pp. 33–44), or carbohydrates (Lotina et al. (1996). Biomaterials, vol. 17, pp. 559–569; Patil et al. (1996). Biomaterials, vol. 17, pp. 2343–2350) as the starting monomers. Both vinyl alcohol and hydroxymethyl acrylate are petroleum-based materials. In many synthesizing reactions carbohydrates are grafted onto the polymer backbone.

Metal recovery from contaminated waste sites, industrial effluents, and spent consumer products is one of the most difficult problems faced by environmental engineers. A system that could bind metals and extract them from aqueous environments is a much desired need. The polymers of the present invention solve the need by providing polymers that are soluble in water and which bind metals in the water producing polymer-metal complexes which then can be extracted into an organic solvent. Specifically, the aforementioned polymers are compositions that are balanced between long hydrocarbon chains and polyamino chains. The hydrocarbon chains pack together to form a two-dimensional lamellar system with the polar polyamino groups on the polar face. Such polymers can bind many transition elements which allows the elements to be extracted into organic solvents such as toluene, chloroform, ether or ethyl acetate with very high efficiency. Examples of metals that can be bound by the polymers are copper II, gold I, silver I, nickel I and iron II and III. The polymers of the present invention when complexed with a metal such as copper and gold and in an organic solvent can be deposited, painted or printed onto circuit boards or microchips to connect various elements. The solvent evaporates leaving behind the metal which can conduct electrical currents. Therefore, the polymers can be used to make conductive tracks on an insulating surface which is highly desirable for microelectronics fabrication such as microchips and circuit boards. Atomic force microscopy demonstrates that the film surface made by the polymers of the present invention is extremely flat, much flatter than can typically be attained by the leading edge technologies of chemical vapor deposition or sputter coating. Chemical vapor deposition and sputter coating require high vacuums, very high temperatures and/or the formation of very reactive species.

The polymers of the present invention represent a major step forward in coating technologies and in preparing planar materials. The polymers of the present invention can be used in the manufacture of marine paints containing metals such as copper. Copper is toxic to the growth of microorganisms and is a desired component of marine paints (Llewellyn (1972). Ann. Occup. Hyg., vol. 15, pp. 393–397). However, marine paints are oil-based and the forms of copper that are soluble in organic solvents in high proportions are difficult to manufacture. Therefore in many marine paints, copper metal is used because soluble forms of copper are not available. Toluene is a common paint solvent and the polymers of the present invention comprising toluene-soluble copper solutions have much promise in manufacture of marine paints especially since the polymers form layers thus increasing the surface availability of the metal. Copper surfaces lead to less fouling than do plastic surfaces in studies involving potable water (Rogers et al. (1994). Appl. Environ. Microbiol., vol. 60, pp. 1585–1592).

The area of water recovery is another area that can benefit from the polymers of the present invention. Polycationic materials such as chitosan are used as flocculants for removal of metal ions, bacteria, and viruses from water (Steinmann and Havemeister (1982). Zentralbl. Bakteriol. Mikrobiol. Hyg. B., vol. 176, pp.546–552). The polymers of the present invention can be used for precious metal and radioactive metal recovery (Onsoyen and Skaugrud (1990). J. Chem. Technol. Biotechnol., vol. 49, pp. 395–404; Muzzarelli and Rocchetti (1974). J. Chromatogr., vol. 96, pp. 115–121), toluene-soluble metal complexes will allow the extraction of transition metal ions into organic solvents.

For purposes of promoting a further understanding of the present invention, the following examples are provided.

EXAMPLE 1

The process using n-octylamine for producing polymers of the present invention which have short chain amines. 2(5H)-furanone (0.84 g. 0.01 mol) was added to a vigorously stirred solution of n-octylamine (1.29 g, 0.01 mol) to form a 1 to 1 mol ratio. Stirring was continued at room temperature until the mixture formed a thick paste. The mixture was then heated at 70° C. for four hours during which time the mixture formed a waxy polymeric solid. $^1$H-NMR spectroscopy in deuterated chloroform showed the disappearance of the signals for furanone between 5.0 and 7.0 ppm and the appearance of new signals between 2.5 and 4.2 ppm representative of the polymer. The signals for the hydroxymethyl group appeared between 3.6 and 4.0 ppm, the methine proton b– to the carbonyl group appeared at 3.45 ppm, the signals for the methylene groups attached to nitrogen appeared at 3.2 ppm, and the methylene protons a– to the carbonyl group appeared between 2.2 and 3.0 ppm. The methylene protons on the alkyl chain β to the nitrogen were at 1.8 ppm, and the other hydrocarbon chain signals appeared upfield from this position. Polymerization was also indicated by the characteristic loss of fine structure on the NMR signals representative of a polymer with the octyl side chains.

EXAMPLE 2

An example using benzylamine for producing polymers of the present invention, which have short chain amines, was performed. 2(5H)-furanone (0.84 g, 0.01 mol) was added to a vigorously stirred solution of benzylamine (1.07 g, 0.01 mol) to form a 1 to 1 mol ratio. The mixture was stirred at room temperature until the mixture formed a thick paste. The mixture was heated to 70° C. for four hours during which time it formed a waxy polymeric solid. $^1$H-NMR spectroscopy in deuterated chloroform showed the disappearance of the signals for furanone between 5.0 and 7.0 ppm and the appearance of new signals between 2.5 and 4.2 ppm representative of the polymer with the benzyl side chains.

EXAMPLE 3

An example using hexylamine for producing polymers of the present invention which have short chain amines was performed. 2(5H)-furanone (0.84 g, 0.01 mol) was added to a vigorously stirred solution of hexylamine (1.01 g, 0.01 mol) to form a 1 to 1 mol ratio. The mixture was stirred at room temperature until the mixture formed a thick paste. The mixture was heated to 70° C. for four hours during which time it formed a waxy polymeric solid. $^1$H-NMR spectroscopy in deuterated chloroform showed the disappearance of the signals for furanone between 5.0 and 7.0 ppm and the appearance of new signals between 2.5 and 4.2 ppm representative of the polymer with the hexyl side chains.

EXAMPLE 4

Figure 5:
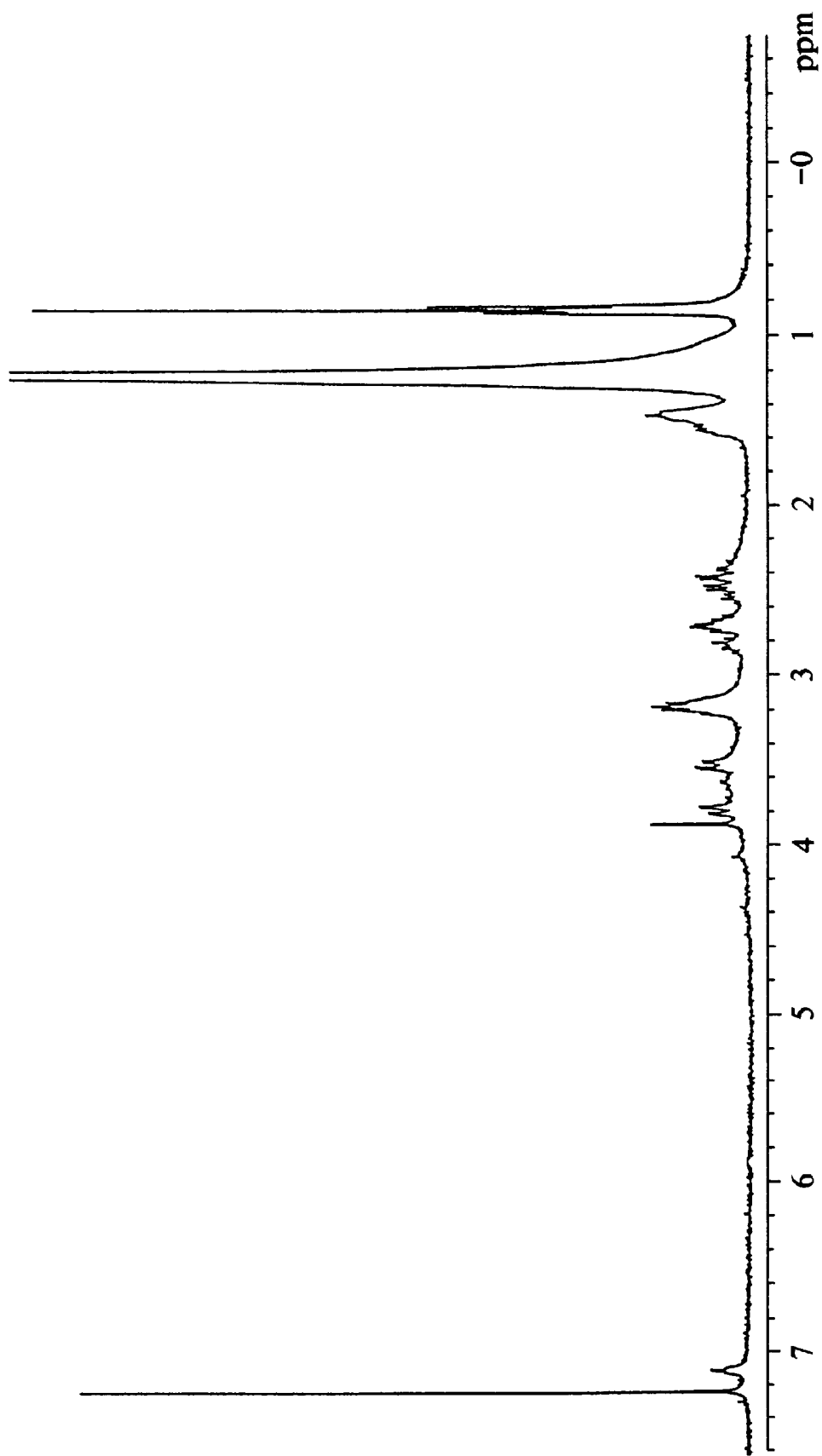
FIG. 5 shows a proton NMR spectrum of 2-D polymer of the present invention synthesized from 2(5H)-furanone and tetradecylamine.

An example using n-tetradecylamine for producing polymers of the present invention which have long chain amines was performed. 2(5H)-furanone (0.84 g, 0.01 mol) was added to a vigorously stirred solution of n-tetradecylamine (2.13 g, 0.01 mol) suspended in 10 ml toluene at 70° C. to form a 1 to 1 mol ratio. The mixture was stirred at 70° C. for four hours after which the toluene was removed by distillation. A very hard polymer was formed by the reaction. $^1$H-NMR spectroscopy in deuterated chloroform was similar to that for octylamine polymer except that the signals were considerably broader and the signals for the n-tetradecyl side chain were much more intense (FIG. 5).

EXAMPLE 5

An example using n-hexadecylamine for producing polymers of the present invention which have long chain amines was performed. 2(5H)-furanone (0.84 g, 0.01 mol) was added to a vigorously stirred solution of n-hexadecylamine (2.41 g, 0.01 mol) suspended in 10 ml of a 1:1 solution of toluene to chloroform (volume/volume) at 70° C. The mixture was stirred at 70° C. for four hours after which the toluene was removed by distillation. A brittle polymer with the n-tetradecyl side chains was formed by the reaction.

EXAMPLE 6

An example using n-octadecylamine for producing polymers of the present invention which have long chain amines was performed. 2(5H)-furanone (0.84 g, 0.01 mol) was added to a vigorously stirred solution of n-octadecylamine (2.69 g, 0.01 mol) suspended in 10 ml of toluene at 70° C. The mixture was stirred at 70° C. for four hours after which the toluene was removed by distillation. A brittle polymer with the n-octadecyl side chains was formed by the reaction.

EXAMPLE 7

An example using glucosamine hydrochloride for producing polymers of the present invention which have very polar amines was performed. 2(5H)-furanone (0.84 g, 0.01 mol) was added to a vigorously stirred solution of glucosamine hydrochloride (2.15 g, 0.01 mol) dissolved in 20 ml of water containing one equivalent of sodium carbonate. The mixture was stirred two hours at room temperature and then at 70° C. for three hours. The reaction mixture was cooled and the polymer product purified by gel filtration on a Biogel P2 (BioRad) column using water as the eluant. The polymer product had glucosyl side chains.

EXAMPLE 8

An example using galactosamine hydrochloride for producing polymers of the present invention which have very polar amines. 2(5H)-furanone (0.84 g, 0.01 mol) was added to a vigorously stirred solution of galactosamine hydrochloride (2.15 g, 0.01 mol) dissolved in 20 ml of water containing one equivalent of sodium carbonate. The mixture was stirred two hours at room temperature and then at 70° C. for three hours. The reaction mixture was cooled and the polymer product purified by gel filtration on a Biogel P2 (BioRad) column using water as the eluant. The polymer product had galactosyl side chains.

EXAMPLE 9

An example using 2-aminoethanol for producing polymers of the present invention which have very polar amines was performed. 2(5H)-furanone (0.84 g, 0.01 mol) was added to a vigorously stirred solution of 2-aminoethanol (0.61 g, 0.01 mol) dissolved in 20 ml of methanol. The mixture was stirred two hours at room temperature and then at 70° C. for three hours. The reaction mixture was cooled and concentrated to dryness yielding a very thick syrup comprising the polymer having hydroxyethyl side chains.

EXAMPLE 10

An example using L-valine to produce an anionic polymer was performed. 1.0 equivalent of sodium hydroxide was added to 0.27 g L-valine in 20 ml of water. Then 2 ml of ethanol was added, followed by 0.25 g (1 equivalent) of furanone. The mixture was stirred at room temperature for 1 hour and then heated at 70° C. for three hours. After three hours, the polymer product was purified by cation exchange chromatography to remove the sodium ions and lyophilized. The polymer product had butylene 5-methyl carboxylic acid side chains.

EXAMPLE 11

An example using L-glycine to produce an anionic polymer was performed. 1.0 equivalent of sodium hydroxide was added to 0.22 g L-valine in 20 ml of water. Then 2 ml of ethanol was added, followed by 0.25 g (1 equivalent) of furanone. The mixture was stirred at room temperature for 1 hour and then heated at 70° C. for three hours. After three hours, the polymer product was purified by cation exchange chromatography to remove the sodium ions and lyophilized. The polymer product had methylene carboxylic acid side chains.

EXAMPLE 12

An example using propionic acid to produce an anionic polymer was performed. 1.0 equivalent of sodium hydroxide was added to 0.22 g propriaonic acid in 20 ml of water. Then 2 ml of ethanol was added, followed by 0.25 g (1 equivalent) of furanone. The mixture was stirred at room temperature for 1 hour and then heated at 70° C. for three hours. After three hours, the polymer product was purified by cation exchange chromatography to remove the sodium ions and lyophilized. The polymer product had propionyl acid side chains.

EXAMPLE 13

An example using pentadecanoic acid to produce an anionic polymer was performed. 1.0 equivalent of sodium hydroxide was added to 0.22 g pentadecanoic acid in 20 ml of water. Then 2 ml of ethanol was added, followed by 0.25 g (1 equivalent) of furanone. The mixture was stirred at room temperature for 1 hour and then heated at 70° C. for three hours. After three hours, the polymer product was purified by cation exchange chromatography to remove the sodium ions and lyophilized. The polymer product had pentadecanyl acid side chains.

EXAMPLE 14

An example for producing an anionic polymer from phosphoethanolamine sodium salt was performed. 1.0 equivalent of sodium hydroxide was added to 1.63 g phosphoethanolamine sodium salt (0.01 mol) in 20 ml of water. Then 2 ml of ethanol was added, followed by 0.25 g (1 equivalent) of furanone. The mixture was stirred at room temperature for 1 hour and then heated at 70° C. for three hours. After three hours, the polymer product was purified by cation exchange chromatography to remove the sodium ions and lyophilized. The polymer had phosphoethanol side chains.

EXAMPLE 15

An example for producing a cross-linked cationic elastomer polymer from pentaethylenehexamine was performed. 2(5H)-furanone (0.2 g) was mixed with 0.553 g (1 equivalent) or 0.227 g (0.5 equivalent) of pentaethylenehexamine in 0.5 ml of ethanol. Upon mixture, a vigorous reaction ensued and the mixtures were then heated at 70° C. for four hours. The products formed from the reaction were gelatinous solids that readily dissolved in water. Polymerization was verified by $^1$H-NMR spectroscopy wherein the signals for the furanone disappeared and a cluster of broad resonances between 2.0 and 4.0 ppm were observed. The elastomers formed could be dissolved in water and acidified with sulfuric acid. Precipitation of the dissolved polymers with acetone yielded an off-white fibrous solid which avidly absorbed several times their weights in water to form a stable gel. The polymer had pentaethylene pentamine side chains.

EXAMPLE 16

An example for producing a mixed side chain polymer was performed. The polymer was soluble in organic solvents but can complex metal ions and anions from which is useful for solubilization of metal ions such as copper II, gold I, silver I, nickel I, and iron II and III in solvents as non-polar as chloroform or toluene.

As an example of typical reaction to form said polymer, 1 g 2(5H)-furanone, 1.27 g tetradecylamine (0.5 equivalents) and 0.553 g pentaethylenehexamine (0.2 equivalents) was used. The furanone was dissolved in 10 ml of chloroform and then the tetradecylamine was added. After complete dissolution of the tetradecylamine, the pentaethylenehexamine was added and the mixture was heated at 70° C. to drive off the chloroform. The heating at 70° C. was then continued for four hours. The polymer had the mixed side chains.

The polymer product was shown to be able to complex metal ions which were then soluble in an organic solvent. In a reaction wherein the polymer was stirred in an aqueous solution of metal ions followed by extraction of the reaction with an organic solvent resulted in the extraction of the metal ions into the organic layer as judged by the color of said layer.

EXAMPLES 17 TO 25

An example of producing a polymer film was performed using the two-dimensional polymers from any one of examples 1 through 9. The polymer of Example 4 was used to make a two-dimensional polymer film. The polymer containing tetradecylamine R groups from Example 4 was dissolved in diethyl ether to form a 0.1% solution. Ten ml of the solution was floated on a water surface contained in a petri dish with a radius of 5 centimeters. The ether was allowed to dry by slow, unforced evaporation after which time a thin film of the two-dimensional polymer was formed on the water surface.

Figure 4A:
FIGS. 4A and 4B show a two-dimensional sheet of a polymeric composition of the present invention.
Figure 4B:
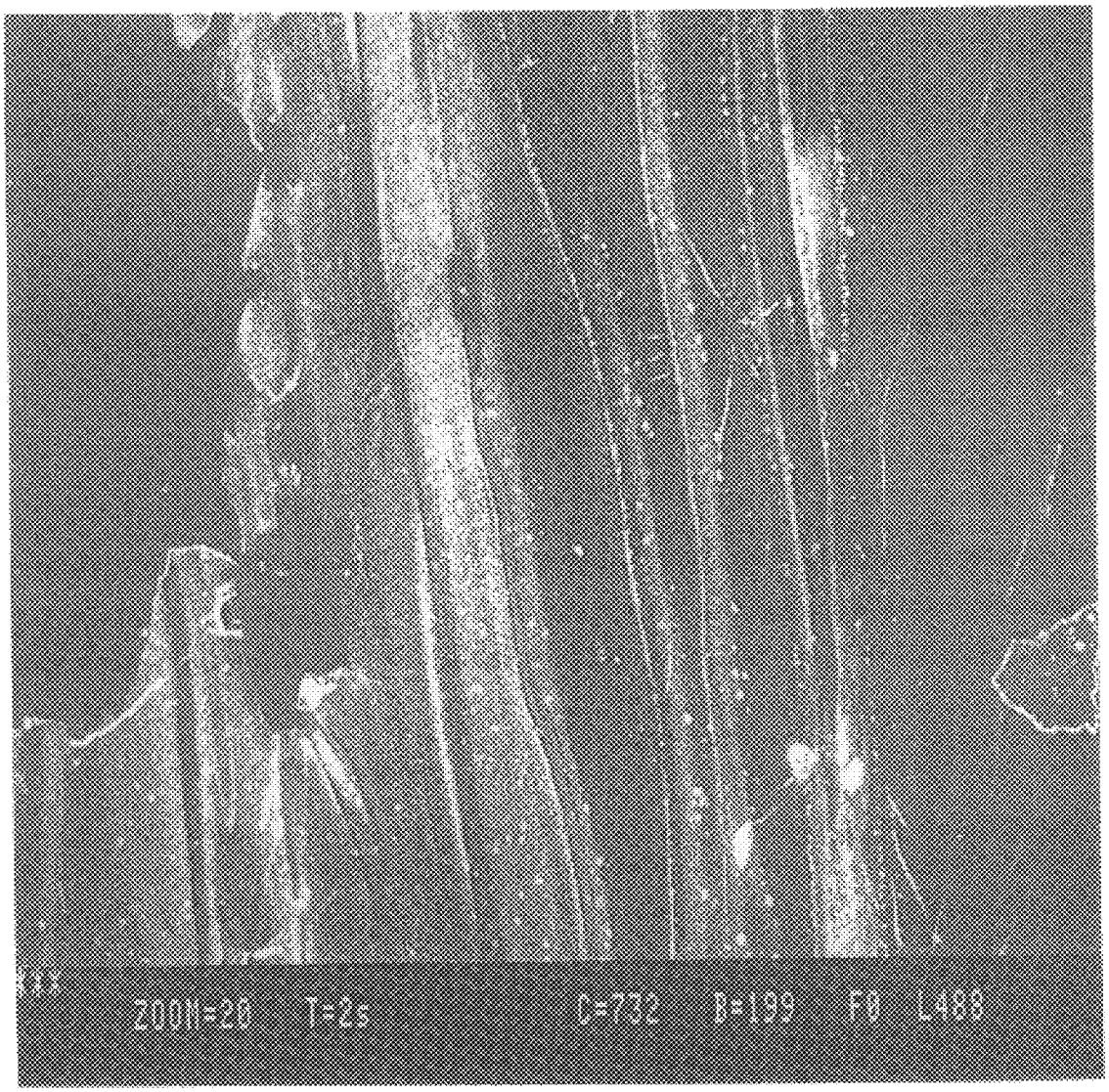

The polymer film was recovered and analyzed by laser scanning confocal microscopy in the phase contrast mode, phase contrast microscopy (FIG. 4A), and in the polarizing mode with crossed polarizers (FIG. 4B). The layered structure of the polymer was readily observable by either technique. In FIG. 4A note the smooth fabric-like texture (the sheet was wrinkled during transfer) and in FIG. 4B note how thin the edges are in comparison to the area. Also note that there is ordering or chain alignment in a top to bottom direction. Similar films were prepared from the polymers from examples 1 through 3, and 5 through 9.

EXAMPLE 26

Two-dimensional polymer compositions of the present invention having a hydrophobic face on one side and a polar poly-cationic face on the other were used to coat materials such as Teflon and polypropylene which were then tested to determine whether said coated materials were thrombogenic and therefore not useful for medical applications such as contact with blood. Applications anticipated are use of the two-dimensional polymers for the preparation of non-thrombogenic surfaces for applications where blood would come in contact with a foreign surface (e.g., an implant or catheter) which would present risk of clotting or coagulation. Results from a Federal Drug Administration (FDA) laboratory approved laboratory using standard FDA-approved protocols showed that materials coated with two-dimensional polymer compositions of the present invention are non-thrombogenic and, in addition, did not result in lysis of red blood cells.

A two-dimensional polymer prepared from n-octylamine, tetradecylamine, pentaethylamine hexamine and 2 (5H)-furanone which had a hydrophobic face on one side and a polar polycationic face on the other was used to coat materials such that the hydrophobic face was adsorbed to the material. The process of coating the material consisted of soaking it in a trough containing the polymer in an ethyl, alcohol and water solution. The polycationic face was then hydrated to form a hydrogel and an interpenetrating gel-layer of Na-heparin was then formed upon the polymer. FIG. 6 is a schematic diagram showing the alkyl chains of the two-dimensional polymer adsorbed to the hydrophobic face of the material (basement substrate) and the polar heads of the polymer forming a hydrogel comprising the anionic heparin gel, interpenetrating gel matrix, and the cationic gel.

The following test was performed to quantitate the thrombogenic potential of materials coated with the two-dimensional polymer of the present invention. The test was a standard recalcification procedure which consisted of measurement of the clotting time of plasma in contact with the material after addition of excess calcium.

The procedure consisted of drawing blood using vacutainers containing 0.1 M sodium citrate at a ratio of 9:1 (blood to anticoagulant). The blood was stored refrigerated until used in the testing which was within four hours of being drawn. Handling of the drawn blood was in compliance with the Department of Labor, Occupational Safety and Health Administration (OSHA), Occupation Exposure to Bloodborne Pathogens, Final Rule Standard, 29 CFR Part 1910.1030. The samples were prepared by immersing 1.8 $cm^2$ sample in plasma. The amount of test material tested was based on USP surface area recommendations or by weight (4.0 g/20 ml extract fluid for polymers and plastic, 2.0 g/20 ml extract fluid for elastomers. Each sample was tested six times. The test reagents were equilibrated at 37° C. for sixty minutes. Samples were prepared in 10×75 mm plastic tubes. Plasma (0.2 ml) and sterile saline (0.2 ml) were added to each sample and control tubes. Samples and control tubes were equilibrated exactly ten minutes. Calcium chloride (0.2 ml) was then added to each test and control tube, gently mixed and held at 37° C. until the sample clotted. The tubes were inspected by gentle tilting every five seconds. The positive control tube contained plasma and sterile saline and glass beads of approximately the same surface area as the tested sample, and the negative control tube contained polypropylene beads of approximately the same surface area as the tested sample. The control and sample tubes were run through the test concurrently.

The average clotting time and standard deviation for the controls are summarized in Table 1, however statistical analysis was not performed using analysis of variance, because the first test sample consisting of polypropylene coated with the present invention did not clot after an average of 1,620 seconds and the second test sample consisting of Teflon coated with the present invention did not clot after an average of 1,645 seconds. In contrast the negative control sample, which consisted of uncoated polyproylene, clotted in 352 averaged seconds and the positive control which consisted of uncoated glass, clotted in 237 averaged seconds. The results show that materials coated in the polymers of the present invention did not demonstrate a shortened clotting time and therefore pose no thrombogenic risk. Moreover, for each test sample the clotting time was lengthened.

TABLE 1

| SAMPLE | CLOT TIME IN SECONDS | | | | | | | Std |
|---|---|---|---|---|---|---|---|---|
| | 1 | 2 | 3 | 4 | 5 | 6 | Ave | Dev |
| Positive control | 215 | 225 | 250 | 255 | 235 | 240 | 237 | 15.1 |
| Negative control | 340 | 380 | 340 | 345 | 325 | 380 | 352 | 23 |

EXAMPLE 27

Two-dimensional polymer compositions of the present invention having a hydrophobic face on one side and a polar poly-cationic face were used to coat materials which were then tested to determine whether said coated materials had hemolytic activity and therefore not useful for applications which required contact with blood.

Applications anticipated are use of the two-dimensional polymers for the preparation of non-hemolytic surfaces for applications where blood would come in contact with a foreign surface (e.g., an implant or catheter). Results from a Federal Drug Administration (FDA) laboratory approved laboratory using standard FDA-approved protocols showed that materials coated with two-dimensional polymer compositions of the present invention are less hemolytic than current materials.

A two-dimensional polymer with a hydrophobic face on one side and a polar polycationic face on the other prepared from n-octylamine, n-tetradecylamine, pentaethylamine tetramine and 2 (5H)-furanone was used to coat material TEFLON® and polypropylene such that the hydrophobic face was adsorbed to the material by soaking the substrate in a trough containing the polymer in an ethyl, alcohol and water solution. The polycationic face was then hydrated to form a hydrogel and an interpenetrating gel-layer of Na-heparin was then formed upon the polymer.

The following was performed to quantitate the hemolytic potential of materials coated with the two-dimensional polymer of the present invention. The test was a standard procedure which consisted of measuring the percent hemolysis of serum in contact with materials coated with said compositions.

The procedure consisted of drawing blood using vacutainers containing 3.8% sodium citrate. The drawn blood was stored refrigerated until used in the testing. Handling of the blood was in compliance with the Department of Labor, Occupational Safety and Health Administration (OSHA), Occupation Exposure to Bloodborne Pathogens, Final Rule Standard, 29 CFR Part 1910.1030. The samples were prepared by immersing 1.8 $cm^2$ sample in plasma. The amount of test material tested was based on USP surface area recommendations or by weight (4.0 g/20 ml extract fluid for polymers and plastic, 2.0 g/20 ml extract fluid for elastomers. Each sample was tested three times. To each test tube 14.7 cm² of sample and 4.9 ml of the physiological saline was added. Then 0.16 ml of blood was added to each tube. The tubes were gently mixed, then incubated at 37° C. for one hour. A hemolytic positive control consisting of 0.1% Na2CO3 in sterile water and a non-hemolytic negative control consisting of uncoated polypropylene beads were included in the test. After incubation, the samples were centrifuged at 500×g and the optical density (OD) of the supernatant fluid was read at 540 nm in a spectrophotometer. The percent hemolysis was interpreted using the following equation:

Percent Hemolysis=T−N/P−N×100

Where T is the test sample OD, N is the negative control OD, and P is the positive control OD.

The results summarized in Table 2 for two experiments show that materials coated with the two-dimensional polymer compositions of the present invention were non-hemolytic. Significantly, both samples coated with the present invention were found to be less hemolytic than the negative control.

TABLE 2

| Sample/Control | OD Readings at 540 nm | |
| --- | --- | --- |
| | 1-Teflon | 2-Polypropylene |
| Sample | 0.020 | 0.017 |
| Positive Control | 2.000 | 2.000 |
| Negative Control | 0.023 | 0.023 |

EXAMPLE 28

This example is a method for metallizing plastic, glass, or other non-metallic surfaces. A two dimensional polymer with hydrocarbon chains on one face and metal ion chelating groups (to which ions are bound) on the other face was prepared from n-octylamine, tetradecylamine, 2(5H)-furanone and pentaethylene hexamine. The polymer was layered (hydrophobic side down) onto the non-metallic surface. The ions are then reduced with a suitable reductant to the free metal which remains as a film on the surface.

FIG. 7 represents a two-dimensional polymer with the alkyl chains adsorbed to a hydrophobic substrate (basement membrane) and complexed to metal ions which are then reduced to the metal. A copper II solution in toluene was prepared and a dried film of a chloroform solution of the polymer was prepared from n-octylamine, tetradecylamine, 2(5H)-furanone and pentaethylene hexamine on the bottom of an Erlenmeyer flask. The solutions when painted onto a glass surface form very even films which are conductive which can be reduced to thin films of copper metal by reacting with dilute borohydride solutions. The metal inhibits biofilm formation.

While the present invention is described herein with reference to illustrated examples, it should be understood that the invention is not limited hereto. Those having ordinary skill in the art and access to the teachings herein will recognize additional modifications and embodiments within the scope thereof. Therefore, the present invention is limited only by the Claims attached herein.

We claim:

1. A process for the preparation of a polyamide polymer which comprises:
   (a) reacting in a single step in a reaction mixture α,β-unsaturated gamma lactone and an amine selected from the group consisting of RNH$_2$ and RNH$_3^+$ and mixtures thereof, wherein R contains between about 1 and 50 carbon atoms alone and is optionally substituted with heteroatoms O, N, S, and P and combinations thereof which allow the formation of a polyamide polymer wherein each of the R can be the same or different in the reaction mixture; and
   (b) separating the polyamide polymer from the reaction mixture, wherein multiple of the R are in vertically aligned spaced relationship along a backbone formed by the polyamide.

2. The process of claim 1 wherein R is selected from the group consisting of alkyl, alkene, alkyne, cycloalkyl, aryl, aralkyl, hydroxyl, nitrile, carboxyl, sulfate, phosphate, sulfonyl, trialkylammonium and combinations thereof and optionally can be substituted with a halogen selected from the group consisting of Cl, I, Br, F and combinations thereof.

3. The process of claim 1 wherein R is the alkyl.

4. The process of claim 1 wherein R is the alkyl containing 1 to 8 carbon atoms and wherein the reaction is conducted in absence of a solvent for the amine.

5. The process of claim 1 wherein R is the alkyl group containing 9 to 30 carbon atoms and wherein the reaction is conducted in the presence of a solvent for the amine.

6. The process of claim 5 wherein the solvent is toluene.

7. The process of claim 1 wherein the amine is alkylene polyamine and wherein the reaction is conducted in the presence of a solvent for the alkylene polyamine.

8. The process of claim 7 wherein the alkylene polyamine is pentaethylene hexamine.

9. The process of claim 8 wherein the solvent is ethanol.

10. The process of claim 7 wherein the alkylene polyamine is admixed with an alkylamine in the reaction mixture.

11. The process of claim 10 wherein the solvent is selected from the group consisting of chloroform and toluene A.

12. A process for the preparation of a polyamide polymer which comprises:
   (a) reacting in a reaction mixture in a single step 2(5H)-furanone and an amine selected from the group consisting of RNH$_2$ and RNH$_3^+$ and mixtures thereof, wherein R contains between about 1 and 50 carbon atoms alone and is optionally substituted with heteroatoms O, N, S, P and combinations thereof which allow the formation of a polyamide polymer wherein each of the R can be the same or different in the reaction mixture of the formula:

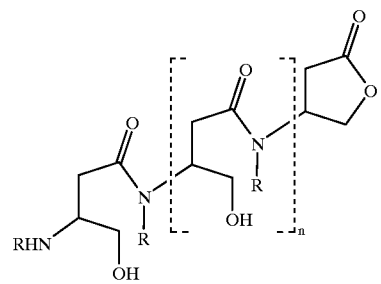

wherein N is between about 50 and 10,000; and
   (b) separating the polyamide polymer from the reaction mixture, wherein multiple of the R are in vertically aligned spaced relationship along a backbone formed by the polyamide.

13. The process of claim 12 wherein R is selected from the group consisting of alkyl, alkene, alkyne, cycloalkyl, aryl, aralkyl, hydroxyl, nitrile, carboxyl, sulfate, phosphate, sulfonyl, trialkylammonium and combinations thereof and optionally can be substituted with a halogen selected from the group consisting of Cl, I, Br, F and combinations thereof.

14. The process of claim 12 wherein R is the alkyl.

15. The process of claim 12 wherein R is the alkyl containing 1 to 8 carbon atoms and wherein the reaction is conducted in absence of a solvent for the amine.

16. The process of claim 12 wherein R is the alkyl group containing 9 to 30 carbon atoms and wherein the reaction is conducted in the presence of a solvent for the amine.

17. The process of claim 16 wherein the solvent is toluene.

18. The process of claim 12 wherein the amine is an alkylene polyamine and wherein the reaction is conducted in the presence of a solvent for the alkylene polyamine.

19. The process of claim 18 wherein the alkylene polyamine in pentaethylene hexamine.

20. The process of claim 19 wherein the solvent is selected from the group consisting of ethanol, other low-molecular weight alcohol, water and tetrahydrofuron, and water and dioxane.

21. A polyamide prepared by reacting in a single step α,β-unsaturated gamma lactone with an amine selected from the group consisting of $RNH_2$ and $RNH_3^+$ and mixtures thereof, wherein R contains between about 1 and 50 carbon atoms and is optionally substituted with heteroatoms O, N, S, P and combinations thereof, wherein multiple of the R are in vertically aligned and spaced relationship along a backbone forming the polyamide and wherein N can be positively charged.

22. The polyamide of claim 21 wherein R is selected from the group consisting of alkyl, alkene, alkyne, cycloalkyl, aryl, aralkyl, hydroxyl, nitrile, carboxyl, sulfate, phosphate, sulfonyl, trialkylammonium and combinations thereof and optionally can be substituted with a halogen selected from the group consisting of Cl, I, Br, F and combinations thereof.

23. The polyamide of claim 21 wherein R is alkyl.

24. The polyamide of claim 21 wherein the alkyl contains 1 to 8 carbon atoms.

25. The polyamide of claim 23 wherein the alkyl contains 9 to 30 carbons.

26. The polyamide of claim 21 wherein R is an alkenyl polyamine group.

27. The polyamide of claim 21 wherein R is a pentaethyleneyl pentamine group.

28. The polyamide of claim 21 wherein R is a mixture of an alkyl group and an alkenyl polyamine group.

29. A polyamide of the formula:

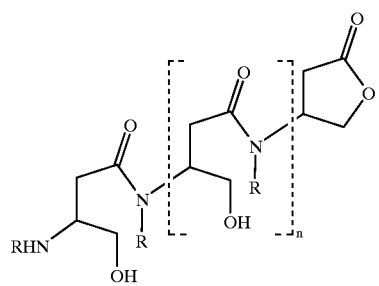

wherein n is between about 50 and 10,000, wherein R is between 1 and 50 carbon atoms alone and is optionally substituted with heteroatoms, oxygen, nitrogen, sulfur, or phosphate and combinations thereof, wherein multiple of the R are in a vertically aligned spaced relationship along a backbone forming the polyamide and wherein R can be positively or negatively charged and prepared by the process of claim 1.

30. The polyamide of claim 29 wherein R is selected from the group consisting of alkyl, alkene, alkyne, cycloalkyl, aryl, aralkyl, hydroxyl, nitrile, carboxyl, sulfate, phosphate, sulfonyl, trialkylammonium and combinations thereof and optionally can be substituted with a halogen selected from the group consisting of Cl, I, Br, F and combinations thereof.

31. The polyamide of claim 29 wherein R is the alkyl.

32. The polyamide of claim 31 wherein the alkyl contains 1 to 8 carbon atoms.

33. The polyamide of claim 31 wherein the alkyl contains 8 to 30 carbon atoms.

34. The polyamide of claim 29 wherein R is an alkenyl polyamine group.

35. The polyamide of claim 29 wherein R is a pentaethyleneyl pentamine group.

36. The polyamide of claim 29 wherein R is a mixture of the alkyl group and a alkenyl polyamine group.

37. The polyamide of claim 29 wherein R contains more than 1 amine or phosphonium group to give the polyamide a positive charge.

38. The polyamide of claim 29 wherein the R contains at least one of the groups selected from the group consisting of carboxyl, sulfate, sulfonate, phosphate and phosphate to give the polyamide a negative charge.

* * * * *

UNITED STATES PATENT AND TRADEMARK OFFICE
CERTIFICATE OF CORRECTION

PATENT NO. : 6,153,724
DATED : November 28, 2000
INVENTOR(S) : Rawle I. Hollingsworth It is certified that error appears in the above-identified patent and that said Letters Patent is hereby corrected as shown below:

Column 2, line 58, "nitrites" should be –nitriles–.

Column 7, line 48, "n functions" should be --$\pi$ functions--.

Column 7, line 59, "nitrites" should be –nitriles–.

Column 9, line 7, "of" after "waterproof" should be deleted.

UNITED STATES PATENT AND TRADEMARK OFFICE
CERTIFICATE OF CORRECTION

PATENT NO. : 6,153,724
DATED : November 28, 2000
INVENTOR(S) : Rawle I. Hollingsworth It is certified that error appears in the above-identified patent and that said Letters Patent is hereby corrected as shown below:

Column 13, line 32, "propriaonic acid" should be -propionic acid-.

Column 17, line 6, "Na2CO3" should be -$Na_2CO_3$-.

Column 20, line 45 (Claim 38), "phosphate" (second occurrence) should be deleted.

Signed and Sealed this

Twenty-ninth Day of May, 2001

Attest:

NICHOLAS P. GODICI

Attesting Officer

Acting Director of the United States Patent and Trademark Office